(12) United States Patent
Hong et al.

(10) Patent No.: US 11,967,114 B2
(45) Date of Patent: Apr. 23, 2024

(54) METHOD AND APPARATUS FOR MEASURING ROBUST CONTINUOUS BLOOD SUGAR USING SKIN IMAGE

(71) Applicant: Research & Business Foundation SUNGKYUNKWAN UNIVERSITY, Suwon-si (KR)

(72) Inventors: Kwang Seok Hong, Suwon-si (KR); Jin Soo Park, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 355 days.

(21) Appl. No.: 17/464,734

(22) Filed: Sep. 2, 2021

(65) Prior Publication Data

US 2022/0067975 A1   Mar. 3, 2022

(30) Foreign Application Priority Data

Sep. 2, 2020   (KR) .......................... 10-2020-0111898

(51) Int. Cl.
  *G06T 7/90*   (2017.01)
  *A61B 5/021*  (2006.01)
  *A61B 5/145*  (2006.01)
  *G06T 7/00*   (2017.01)

(52) U.S. Cl.
  CPC ............ *G06T 7/90* (2017.01); *A61B 5/02108* (2013.01); *A61B 5/14532* (2013.01); *G06T 7/0012* (2013.01); *G06T 2207/20081* (2013.01); *G06T 2207/30088* (2013.01)

(58) Field of Classification Search
  CPC ................. G06T 7/90; G06T 7/0012; G06T 2207/20081; G06T 2207/30088; A61B 5/02108; A61B 5/14532
  USPC ....................................................... 382/128
  See application file for complete search history.

(56) References Cited

U.S. PATENT DOCUMENTS

| 2014/0273858 A1* | 9/2014 | Panther ................ A61B 5/1123 455/41.2 |
| 2015/0216482 A1* | 8/2015 | Kasahara ............. A61B 5/1455 600/316 |
| 2015/0287187 A1* | 10/2015 | Redtel ................... G06T 7/0016 382/128 |

FOREIGN PATENT DOCUMENTS

| JP | 2019-141414 A | 8/2019 |
| KR | 10-2015-0095661 A | 8/2015 |
| KR | 10-2018-0028823 A | 3/2018 |
| KR | 10-2018-0042657 A | 4/2018 |
| KR | 10-2019-0007803 A | 1/2019 |

* cited by examiner

Primary Examiner — Michael R Neff
(74) Attorney, Agent, or Firm — NSIP Law

(57) ABSTRACT

A method for measuring blood sugar that is performed by an apparatus for measuring blood is provided. The method includes calculating color data from multiple skin regions of interest in a skin image, classifying a user's meal state into a pre-meal state or a post-meal state through analysis of acquired user information, estimating blood sugar by applying the calculated color data to a blood sugar regression linear equation corresponding to the classified user's meal state, and measuring robust blood sugar by weighted averaging the estimated blood sugar.

20 Claims, 13 Drawing Sheets

METHOD AND APPARATUS FOR MEASURING ROBUST CONTINUOUS BLOOD SUGAR USING SKIN IMAGE

CROSS-REFERENCE TO RELATED APPLICATION

This application claims priority to Korean Patent Application No. 10-2020-0111898, filed on Sep. 2, 2020. The entire contents of the application on which the priority is based are incorporated herein by reference.

TECHNICAL FIELD

The present disclosure relates to a method and an apparatus for measuring robust continuous blood sugar using a skin image.

BACKGROUND

Diabetes is a chronic disease that occurs a great deal in modern people. In the Republic of Korea, more than 5 million people, corresponding to 10% of the total population, have diabetes. The onset of diabetes is due to insulin produced in the pancreas being absolutely or relatively insufficient due to various causes such as obesity, stress, poor eating habits, and congenital heredity, and thus a balance of sugar in blood cannot be corrected, resulting in high sugar content in the blood.

Blood usually contains a certain concentration of glucose, and tissue cells obtain energy from glucose. However, when glucose increases more than necessary, the glucose is not properly stored in liver, muscle, fat cells, or the like and is accumulated in the blood. As a result, diabetic patients maintain much higher blood sugar than normal people. As excess blood sugar passes through tissues and is excreted in urine, sugar, which is absolutely necessary for each tissue in the body, becomes insufficient, causing abnormalities in each tissue of the body.

Diabetes is rarely asymptomatic in its early onset. As diabetes progresses, diabetes-specific symptoms such as polyphagia, polyuria, weight loss, general malaise, itchy skin, and long-lasting wounds on hands and feet appear. As diabetes progresses further, complications that progress to visual impairment, hypertension, kidney disease, stroke, periodontal disease, muscle spasms, neuralgia, gangrene, or the like appear. In order to diagnose diabetes and manage diabetes to prevent diabetes from progressing to complications, systematic blood sugar measurement and treatment should be performed in parallel.

The market for blood sugar measuring instruments is continuously growing due to the rapid increase in the number of diabetic patients worldwide. In order to efficiently manage diabetic patients who need lifelong management, the market demand for non-invasive blood sugar measuring instruments that can measure blood sugar at all times without pain is increasing. Accordingly, many medical device manufacturers provide various types of portable blood sugar measuring instruments to measure blood sugar at home.

A lot of research and development is being conducted for non-invasive blood sugar measuring instruments. However, the technical difficulty of the non-invasive blood sugar measuring instruments is very high, so long-term R&D investment in hardware and software is necessary to secure the accuracy and reliability of commercial technology. In addition, as eating habits and lifestyles become westernized around the world, advanced diseases such as diabetes and obesity are increasing, resulting in an increase in socioeconomic costs. In order to reduce the social burden caused by diabetes, the need to develop blood sugar measuring instruments with an innovative technique instead of the existing blood collecting type blood sugar measuring instruments is emerging.

Reviewing the invasive blood sugar measurement, two products, Medtronic's Guardian Connect and Dexcom's G5 are dominating the market for blood sugar measuring instruments that is growing rapidly recently. Although i-SENS, Inc., a company in the Republic of Korea, has reached the product development completion stage, a method developed by i-SENS is a minimally invasive method that uses a microneedle to measure blood sugar when collecting blood, and causes pain accordingly.

Reviewing the non-invasive blood sugar measurement, various body fluids (tears, sweat, saliva, urine, etc.) based blood sugar measuring instruments are being developed due to the difficulty of the non-invasive blood sugar measurement technology. However, there is a disadvantage in that there is a time delay in reflecting the actual change in levels of sugar present in various body fluids for measuring blood sugar, resulting in lowering the utility in the market.

SUMMARY

In order to reduce the conventional problems and replace the blood sugar measuring instrument, embodiments of the present disclosure are for providing a method and apparatus for measuring robust continuous blood sugar using a skin image allowing the robust continuous blood sugar to be measured using the skin image at all times and continuously in a non-invasive/contactless/non-invasive manner by using a general camera, an infrared camera, a zoom camera, or a wearable device owned by a user without installing additional hardware modules, and suggesting and managing a method of diagnosing a blood sugar state by analysis of change in user's blood sugar and controlling blood sugar.

However, the problems to be solved by the present disclosure are not limited thereto, and may be variously extended even in an environment within a range not departing from the spirit and scope of the present disclosure.

In accordance with an aspect of the present disclosure, there is provided a method for measuring blood sugar, which is performed by an apparatus for measuring blood, the method including: calculating color data from multiple skin regions of interest in a skin image; classifying a user's meal state into a pre-meal state or a post-meal state through analysis of acquired user information; estimating blood sugar by applying the calculated color data to a blood sugar regression linear equation corresponding to the classified user's meal state; and measuring robust blood sugar by weighted averaging the estimated blood sugar.

The method may further include diagnosing a blood sugar state by analyzing a change in user's blood sugar.

The method may further include providing a blood sugar control method according to the diagnosed blood sugar state.

The method may further include calculating a blood pressure and a stress index using a pulse wave signal calculated through the calculated color data.

Further, the acquired user information may include meal time and at least one of gender, age, height, weight, and sleep time.

Further, the estimating of the blood sugar may include applying the calculated color data to a first pre-meal blood sugar regression linear equation to estimate first pre-meal blood sugar.

Further, the estimating of the blood sugar may include bias-adjusting the estimated first pre-meal blood sugar using the acquired user information to estimate bias-adjusted second pre-meal blood sugar.

Further, the estimating of the blood sugar may include applying the estimated second pre-meal blood sugar to a second pre-meal blood sugar regression linear equation to estimate third pre-meal blood sugar.

Further, the estimating of the blood sugar may include applying the calculated color data to a first post-meal blood sugar regression linear equation to estimate first post-meal blood sugar.

Further, the estimating of the blood sugar may include bias-adjusting the estimated first post-meal blood sugar using the acquired user information to estimate bias-adjusted second post-meal blood sugar.

Further, the estimating of the blood sugar may include applying the estimated second post-meal blood sugar to a second post-meal blood sugar regression linear equation to estimate third post-meal blood sugar.

The method may further include calculating a multiple regression equation by applying multiple regression analysis to pre-meal/post-meal blood sugar based on the skin image, user's body information, and measurement environment information to obtain a multiple regression equation based on a user behavior pattern, blood sugar measured based on the skin image, and measurement environment log data; and constructing a blood sugar regression equation database that stores blood sugar regression equation data bias-adjusted according to the user's body information and the measurement environment information using the calculated multiple regression equation.

The method may further include confirming the user's body information through image recognition; estimating a meal time by analyzing the user behavior pattern, and classifying a user's meal state into a pre-meal state or a post-meal state based on the estimated meal time; and measuring robust blood sugar bias-adjusted according to the measurement environment information using the blood sugar regression equation, which is bias-adjusted according to the user's body information and the measurement environment information, and the skin image.

In accordance with another aspect of the present disclosure, there is provided an apparatus for measuring robust continuous blood sugar using a skin image, the apparatus including: an image acquisition module configured to acquire the skin image including multiple skin regions of interest; a memory configured to store one or more programs; and a processor configured to execute the stored one or more programs. Further, the processor calculates color data from the multiple skin regions of interest in the acquired skin image, classifies a user's meal state into a pre-meal state or a post-meal state through analysis of acquired user information, estimates blood sugar by applying the calculated color data to a blood sugar regression linear equation corresponding to the classified user's meal state, and weighted averages the estimated blood sugar to measure robust blood sugar.

Further, the processor may diagnose a blood sugar state by analyzing a change in user's blood sugar.

Further, the processor may provide a blood sugar control method according to the diagnosed blood sugar state.

Further, the processor may estimate first pre-meal blood sugar by applying the calculated color data to a first pre-meal blood sugar regression linear equation, estimate bias-adjusted second pre-meal blood sugar by bias-adjusting the estimated first pre-meal blood sugar using the acquired user information, and apply the estimated second pre-meal blood sugar to a second pre-meal blood sugar regression linear equation to estimate third pre-meal blood sugar.

Further, the processor may estimate first post-meal blood sugar by applying the calculated color data to a first post-meal blood sugar regression linear equation, estimate bias-adjusted second post-meal blood sugar by bias-adjusting the estimated first post-meal blood sugar using the acquired user information, and apply the estimated second post-meal blood sugar to a second post-meal blood sugar regression linear equation to estimate third post-meal blood sugar.

Further, the processor may calculate a multiple regression equation by applying multiple regression analysis to pre-meal/post-meal blood sugar based on the skin image, user's body information, and measurement environment information to obtain a multiple regression equation based on a user behavior pattern, blood sugar measured based on the skin image, and measurement environment log data, construct a blood sugar regression equation database that stores blood sugar regression equation data bias-adjusted according to the user's body information and the measurement environment information using the calculated multiple regression equation, confirm the user's body information through image recognition, estimate a meal time by analyzing the user behavior pattern and classifies the user's meal state into the pre-meal state or the post-meal state based on the estimated meal time, and measure the robust blood sugar bias-adjusted according to the measurement environment information using the blood sugar regression equation, which is bias-adjusted according to the user's body information and the measurement environment information, and the skin image.

In accordance with still another aspect of the present disclosure, there is provided a non-transitory computer-readable storage medium storing computer-executable instructions which cause, when executed by a processor, the processor to perform a method that includes: calculating color data from multiple skin regions of interest in the skin image; classifying a user's meal state into a pre-meal state or a post-meal state through analysis of acquired user information; estimating blood sugar by applying the calculated color data to a blood sugar regression linear equation corresponding to the classified user's meal state; and weighted averaging the estimated blood sugar to measure robust blood sugar.

The disclosed technology can have the following effects. However, since a specific embodiment is not construed as including all of the following effects or only the following effects, it should not be understood that the scope of the disclosed technology is limited to the specific embodiment.

According to the embodiments of the present disclosure, it is possible to suggest a contactless/non-invasive/imperceptible/painless measurement method that does not require blood collection for measurement of blood sugar without additional costs by measuring the blood sugar only by installing software on a smart device equipped with a camera owned by a user instead of the existing non-invasive blood sugar measurement method.

In addition, according to the embodiments of the present disclosure, it is possible to manage blood sugar by suggesting a method of diagnosing a user's blood sugar state and controlling blood sugar by not only measuring the blood sugar but also monitoring the blood sugar using color data of a skin image.

DETAILED DESCRIPTION

Figure 1:
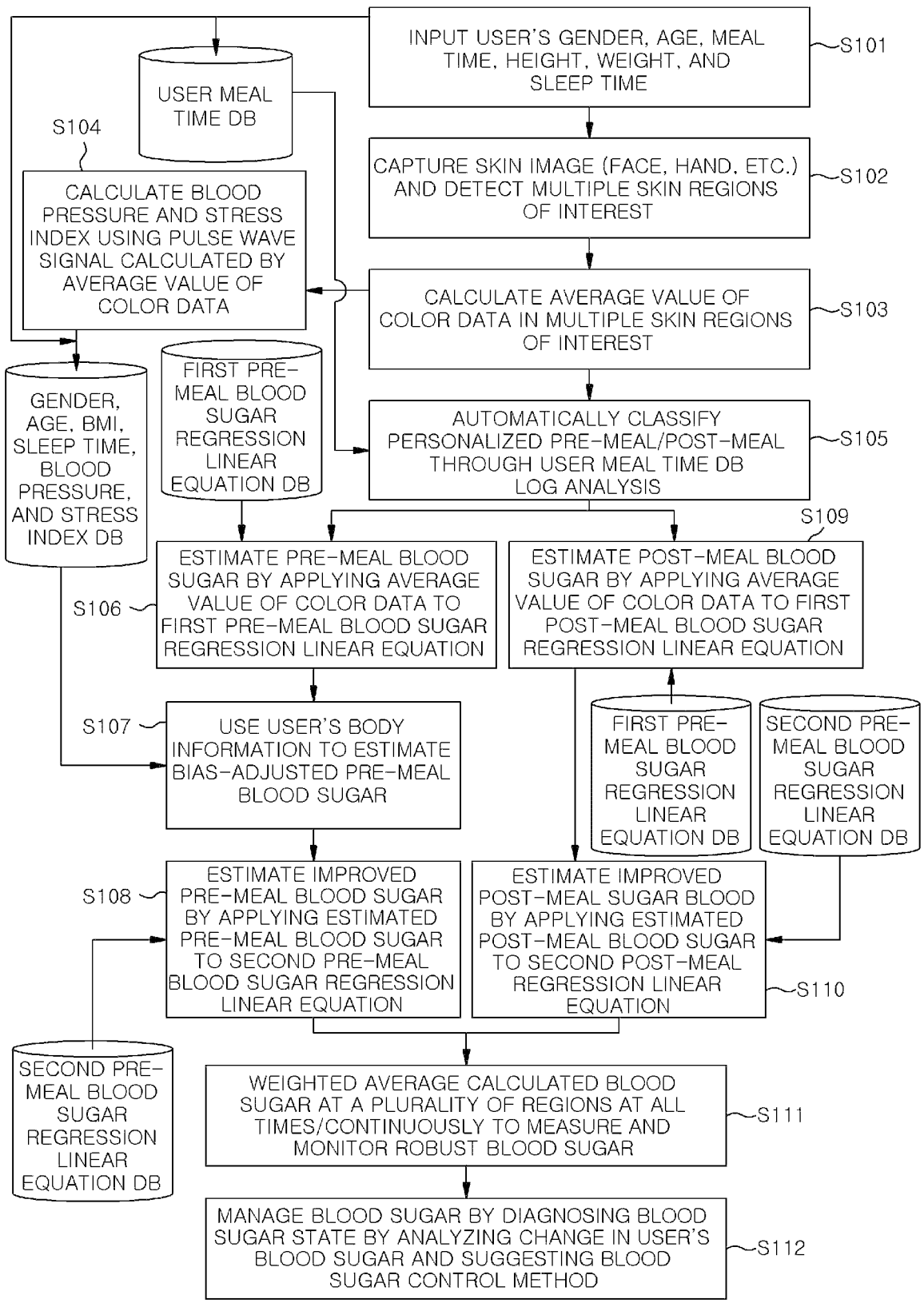
FIG. 1 is an overall flowchart of a method of measuring robust continuous blood sugar using a skin image according to an embodiment of the present disclosure.

The present disclosure may be variously modified in various forms and may have various exemplary embodiments, and specific exemplary embodiments will be illustrated in the drawings and described in detail. However, it should be appreciated that the present disclosure is not limited to the specific exemplary embodiments and all modifications, equivalents and/or alternatives thereof also belong to the scope of the present disclosure. In the following description of exemplary embodiments of the present disclosure, the detailed descriptions of known functions or configurations incorporated herein will be omitted when it is determined that the detailed descriptions may unnecessarily obscure the subject matter of embodiments of the present disclosure.

Terms such as "first" and "second" may be used to describe various constituting elements, but the constituting elements should not be limited by the terms. The terms are introduced to distinguish one element from the others.

The terms used in the present application are only used for describing specific embodiments, and are not intended to limit the present disclosure. Unless otherwise defined, all terms used in the present specification, including technical or scientific terms, have the same meaning as commonly understood by one of ordinary skill in the art to which the present disclosure belongs. Terms such as those defined in commonly used dictionaries should be interpreted as having a meaning consistent with the meaning in a context of the related technology, and should not be interpreted as an ideal or excessively formal meaning unless explicitly defined in this application.

Singular expressions include plural expressions unless the context clearly indicates otherwise. In the present application, terms such as "comprise" or "have" are intended to designate the presence of features, numbers, steps, operations, components, parts, or combinations thereof described in the specification, but it should be understood that they do not preclude in advance the possibility of the presence or addition of one or more other features, numbers, steps, operations, components, parts, or combinations thereof.

Hereinafter, preferred embodiments of the present disclosure will be described in more detail with reference to the accompanying drawings. In describing the present disclosure, the same reference numerals will be given to the same components in the drawings, and redundant descriptions thereof will be omitted.

An embodiment of the present disclosure relates to a method of managing a blood sugar by suggesting a contact-less/non-invasive/imperceptible/painless blood sugar estimation method using skin images (face, hand, etc.) at all times/continuously and a method of diagnosing a blood sugar state and controlling blood sugar through monitoring. Conventionally, blood sugar was measured using a blood sugar measuring instrument based on various body fluids (tears, sweat, saliva, urine, etc.) for non-invasive measurement of blood sugar. On the other hand, an embodiment of the present disclosure uses wearable devices (such as a wristwatch type, body (ear, face, etc.) attachment type, etc.) as well as a general camera, an infrared camera, and a zoom camera without a hardware module for additional blood sugar measurement to measure blood sugar at all times/continuously.

In detail, an embodiment of the present disclosure provides a general camera, an infrared camera, a zoom camera, a wearable device, or the like that a user owns after the user inputs gender, age, meal time (breakfast, lunch, and dinner), height, weight, and sleep time, etc., by using a zoom camera or a wearable device, etc., to capture a skin image in a contactless/non-invasive/imperceptible/painless manner, and detect multiple skin regions of interest (ROI). According to an embodiment of the present disclosure, an average value of $C_r$ and $C_o$ color data is calculated by converting an red/green/blue (RGB) color system of the detected multiple skin regions of interest ($ROI_1$, $ROI_2$, etc.) into $YC_gC_o$ and $YC_bC_r$ color systems. According to an embodiment of the present disclosure, a pulse wave signal may be calculated by analyzing a change in color data calculated in the skin ROI, and a blood pressure, a stress index, or the like may be calculated using the calculated pulse wave signal.

According to an embodiment of the present disclosure, when a user's blood sugar measurement time is pre-meal, the average value of the $C_rC_o$ color data, to which a weighted average is applied, is applied to a "first pre-meal blood sugar regression linear equation" to estimate an initial pre-meal (breakfast, lunch, and dinner) blood sugar, user's body information (gender, age, body mass index (BMI), sleep time, blood pressure, and stress index) is used to estimate the bias-adjusted pre-meal blood sugar, and the estimated pre-meal blood sugar (bias-adjusted pre-meal blood sugar) is applied to a "second pre-meal blood sugar regression linear equation" to estimate the improved pre-meal blood sugar.

According to an embodiment of the present disclosure, when the user's blood sugar measurement time is post-meal, the average value of the $C_rC_o$ color data, to which the weighted average is applied, is applied to a "first post-meal blood sugar regression linear equation" to estimate post-meal (breakfast, lunch, and dinner) blood sugar, and the estimated post-meal blood sugar is applied to a "second post-meal blood sugar regression linear equation" to estimate improved post-meal blood sugar.

According to an embodiment of the present disclosure, by storing a meal time input by a user when measuring blood sugar in a "meal time database (DB)", and periodically analyzing a log of the stored user's "meal time DB", it is possible to perform personalized pre-meal/post-meal automatic classification. In addition, according to an embodiment of the present disclosure, robust blood sugar may be measured by weighted averaging of blood sugar (pre-meal or post-meal) estimated at multiple sites at all times/continuously.

An embodiment of the present disclosure provides a method of measuring blood sugar using the average data of the $C_rC_o$ color data to which the weighted average calculated in the skin image is applied, and furthermore, by adopting the same method, the blood sugar may be measured using various color systems of the skin region of interest.

FIG. 1 is an overall flowchart of a method of measuring robust continuous blood sugar using a skin image according to an embodiment of the present disclosure.

In step S101, an apparatus for measuring blood sugar according to an embodiment of the present disclosure receives a user's gender, age, meal time, height, weight, and sleep time from a user.

In step S102, the apparatus for measuring blood sugar captures a skin image (face, hand, etc.) using a camera of a smart device and detects multiple skin ROIs (ROI1, ROI2, etc.). The apparatus for measuring blood sugar may capture skin images in a contactless/non-invasive/imperceptible/painless manner using a general camera, an infrared camera, a zoom camera, a wearable device, or the like that a user owns.

In step S103, the apparatus for measuring blood sugar converts the RGB color system designated as one of various color systems in the detected multiple skin ROIs into the $YC_gC_o$ and $YC_bC_r$ color systems to calculate $C_r$ and $C_o$ color data and calculate the average value of the $C_rC_o$ color data to which the weighted average is applied.

In step S104, the apparatus for measuring blood sugar calculates a blood pressure and a stress index using a pulse wave signal calculated through the average value of the $C_rC_o$ color data to which the weighted average is applied. Here, the input user's gender, age, height, weight, and sleep time and the calculated blood pressure and stress index are stored in a DB for the user's gender, age, BMI, sleep time, blood pressure, and stress index.

In step S105, the apparatus for measuring blood sugar may store a meal time input by a user when measuring blood sugar in a 'meal time DB', and periodically analyzes a log of the stored user's 'meal time DB' to perform personalized pre-meal/post-meal automatic classification.

In step S106, the apparatus for measuring blood sugar applies the average value of the $C_rC_o$ color data, to which a weighted average is applied, to a "first pre-meal blood sugar regression linear equation" when the user's blood sugar measurement time is pre-meal to estimate initial pre-meal (breakfast, lunch, and dinner) blood sugar.

In step S107, the apparatus for measuring blood sugar estimates bias-adjusted pre-meal blood sugar using the user's body information (gender, age, BMI, sleep time, blood pressure, and stress index).

In step S108, the apparatus for measuring blood sugar applies the estimated pre-meal blood sugar (bias-adjusted pre-meal blood sugar) to the "second pre-meal blood sugar regression linear equation" to estimate improved pre-meal blood sugar.

Meanwhile, in step S109, the apparatus for measuring blood sugar applies the average value of the $C_rC_o$ color data, to which the weighted average is applied, to a "first post-meal blood sugar regression linear equation" when the user's blood sugar measurement time is post-meal to estimate post-meal (breakfast, lunch, and dinner) blood sugar.

In step S109, the apparatus for measuring blood sugar applies the estimated post-meal blood sugar to the "second post-meal blood sugar regression linear equation" to estimate improved post-meal blood sugar.

According to an embodiment of the present disclosure, the skin ROI of the skin image specified in the embodiment of the present disclosure may be designated as left and right cheek regions where facial arteries are located, and even in other regions, the improved blood sugar regression equation may be estimated using the blood sugar DB and the designated color system average DB in the same area.

In addition, in step S111, the apparatus for measuring blood sugar may measure robust blood sugar by weighted averaging of blood sugar (pre-meal or post-meal) estimated at multiple regions at all times/continuously.

In addition, in step S112, the apparatus for measuring blood sugar may be managed by suggesting a method of diagnosing a blood sugar state and controlling blood sugar based on the change in user's blood sugar analyzed through monitoring.

Figure 2:
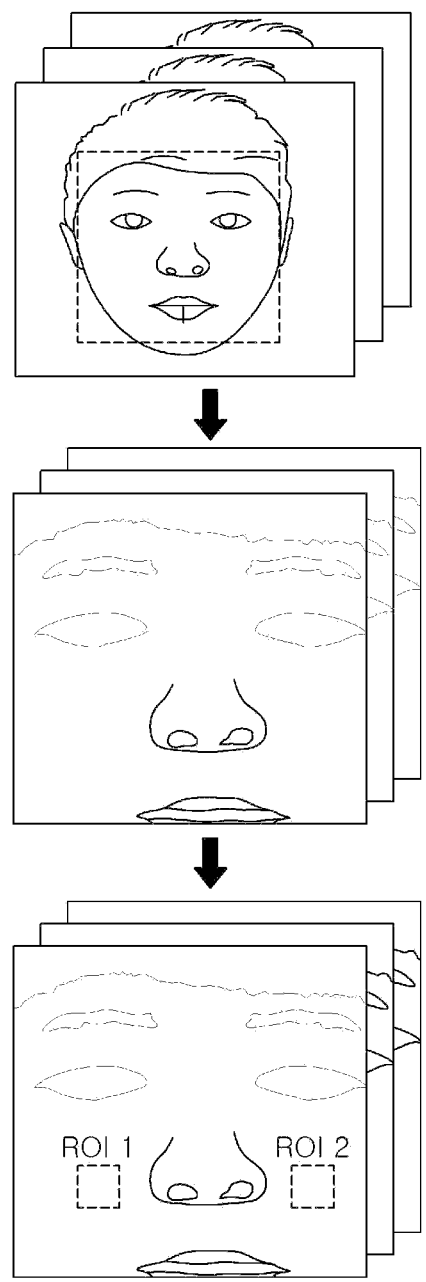
FIGS. 2 and 3 are diagrams illustrating detection of a skin region of interest and an average value of color data in the method of measuring robust continuous blood sugar using a skin image according to the embodiment of the present disclosure.
Figure 3:
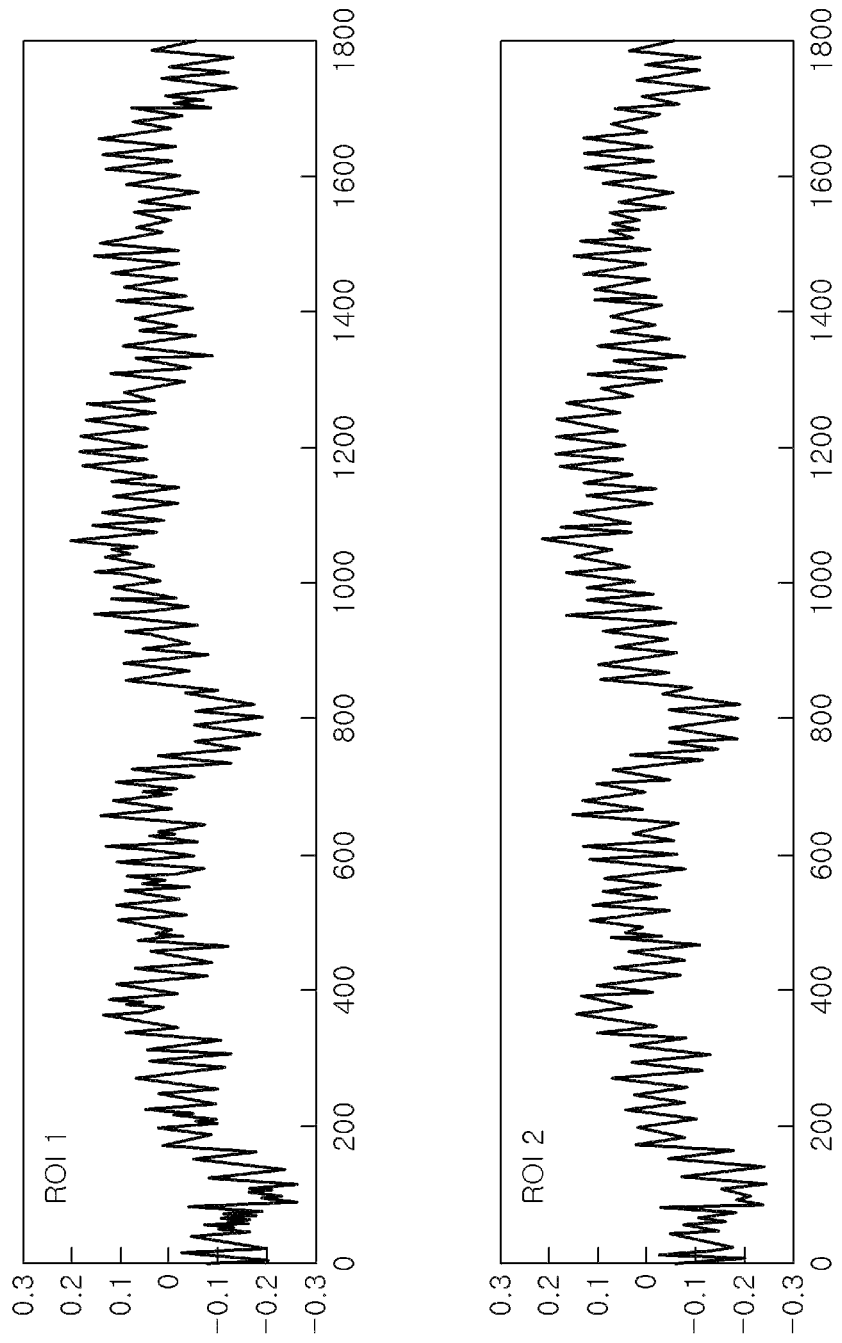

FIGS. 2 and 3 are diagrams illustrating detection of the skin region of interest and the average value of the color data in the method of measuring robust continuous blood sugar using a skin image according to the embodiment of the present disclosure.

As illustrated in FIG. 2, the apparatus for measuring blood sugar detects multiple skin ROIs (ROI1, ROI2, etc.) from a skin image captured using a smart device equipped with a camera and converts the RGB color system of the skin region to the $YC_gC_o$ and $YC_bC_r$ color systems to calculate $C_r$ and $C_o$.

The apparatus for measuring blood sugar applies the average value of the $C_rC_o$ color data to which the weighted average illustrated in FIG. 3 is applied to the "first pre-meal blood sugar regression linear equation" when the user's blood sugar measurement time is pre-meal to estimate the initial pre-meal (breakfast, lunch, and dinner) blood sugar, uses the user's body information (gender, age, BMI, sleep time, blood pressure, and stress index) to estimate the bias-adjusted pre-meal blood sugar, and applies the estimated pre-meal blood sugar (bias-adjusted pre-meal blood sugar) to the "second pre-meal blood sugar regression linear equation" to estimate the improved pre-meal blood sugar.

The apparatus for measuring blood sugar applies the average value of the $C_rC_o$ color data to which the weighted average is applied to the "first post-meal blood sugar regression linear equation" when the user's blood sugar measurement time is post-meal to estimate the post-meal (breakfast, lunch, and dinner) blood sugar, and applies the estimated post-meal blood sugar to the "second post-meal blood sugar regression linear equation" to estimate the improved post-meal blood sugar.

In addition, the apparatus for measuring blood sugar may measure robust blood sugar by weighted averaging of blood sugar (pre-meal or post-meal) estimated at multiple regions at all times/continuously. In addition, the apparatus for measuring blood sugar may be managed by suggesting a method of diagnosing a blood sugar state and controlling blood sugar based on the change in user's blood sugar analyzed through monitoring.

Figure 4:
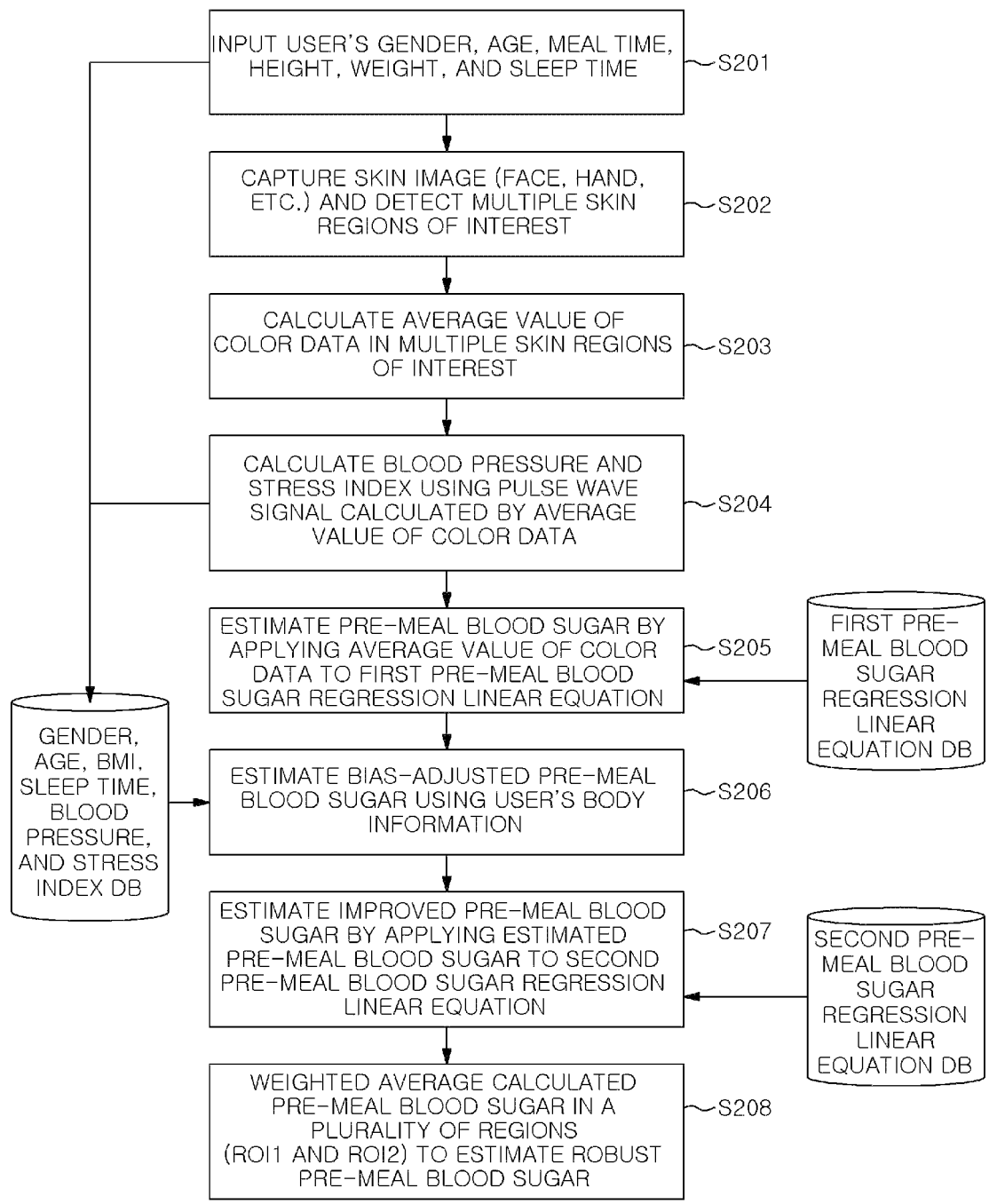
FIG. 4 is a flowchart illustrating a process of estimating pre-meal blood sugar using a skin image in the method of measuring robust continuous blood sugar using a skin image according to the embodiment of the present disclosure.

FIG. 4 is a flowchart illustrating a process of estimating pre-meal blood sugar using a skin image in the method of measuring robust continuous blood sugar using a skin image according to the embodiment of the present disclosure.

In step S201, the apparatus for measuring blood sugar according to an embodiment of the present disclosure receives a user's gender, age, meal time, height, weight, and sleep time from a user.

In step S202, the apparatus for measuring blood sugar captures a skin image using a camera of a smart device and detects multiple skin ROIs (ROI1, ROI2, etc.).

In step S203, the apparatus for measuring blood sugar converts the RGB color system designated as one of the various color systems in the detected skin ROI into the $YC_gC_o$ and $YC_bC_r$ color systems to calculate $C_r$ and $C_o$ and calculate the average value of the $C_rC_o$ color data to which the weighted average is applied.

In step S204, the apparatus for measuring blood sugar calculates a blood pressure and a stress index using a pulse wave signal calculated through the average value of the color data. Here, the input user's gender, age, height, weight, and sleep time, and the calculated blood pressure and stress index are stored in the DB for the user' gender, age, BMI, sleep time, blood pressure, and stress index.

In step S205, the apparatus for measuring blood sugar applies the average value of the $C_rC_o$ color data, to which the weighted average is applied, to the "first pre-meal blood sugar regression linear equation" to estimate the pre-meal blood sugar.

In step S206, the apparatus for measuring blood sugar estimates bias-adjusted pre-meal blood sugar using the user's body information (gender, age, BMI, sleep time, blood pressure, and stress index).

In step S207, the apparatus for measuring blood sugar applies the estimated pre-meal blood sugar to the "second pre-meal blood sugar regression linear equation" to estimate the improved pre-meal blood sugar.

In step S208, the apparatus for measuring blood sugar may measure the robust pre-meal blood sugar by weighted averaging of the pre-meal blood sugar estimated at multiple regions at all times/continuously.

Figure 5:
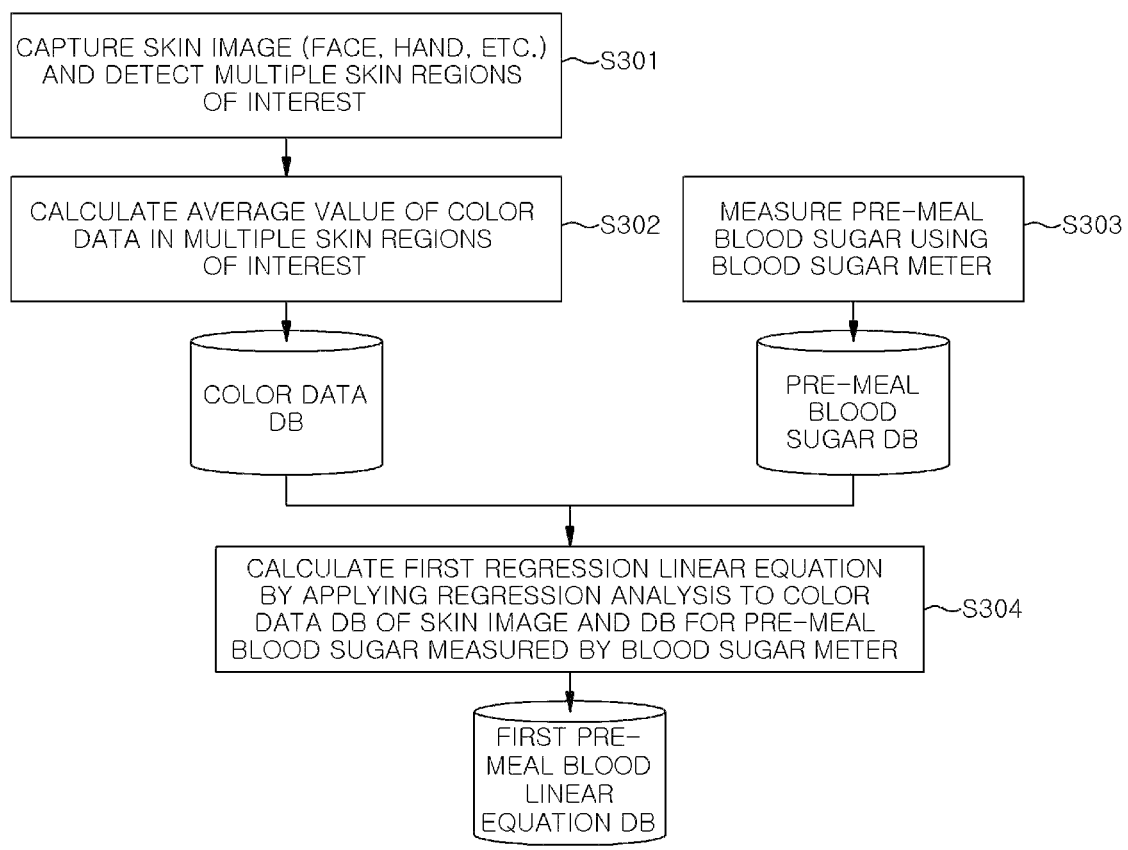
FIG. 5 is a flowchart illustrating a process of calculating a first pre-meal blood sugar measurement regression linear equation and storing the calculated first pre-meal blood sugar measurement regression linear equation in a database (DB) for a first pre-meal blood sugar regression linear equation in the method of measuring robust continuous blood sugar using a skin image according to the embodiment of the present disclosure.
Figure 6:
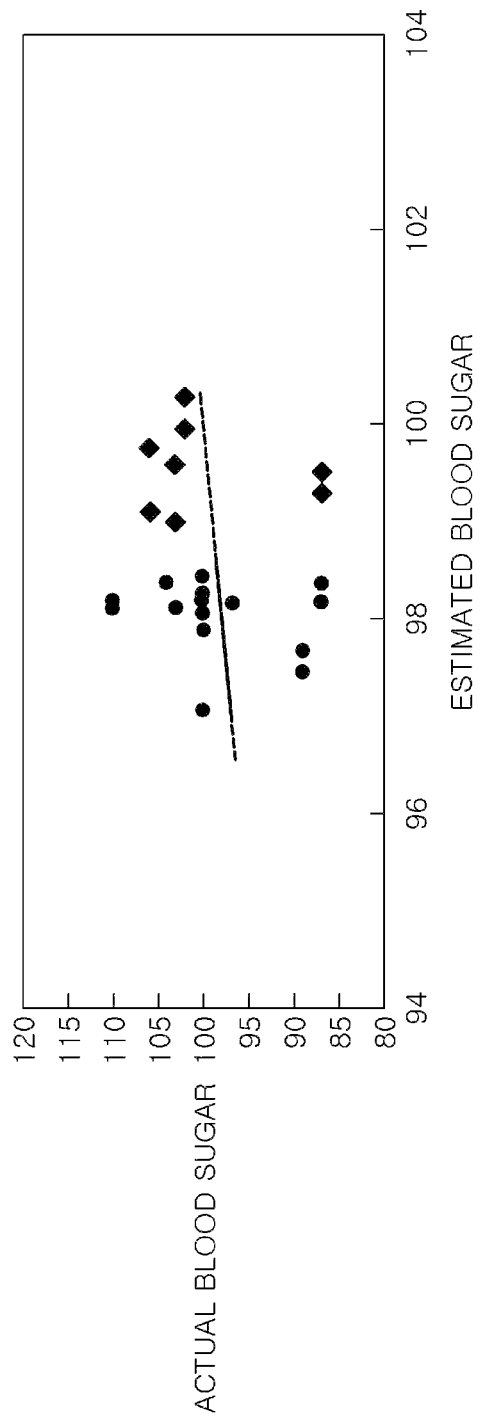
FIG. 6 is a diagram illustrating the first pre-meal blood sugar regression linear equation.

FIG. 5 is a flowchart illustrating a process of calculating a first pre-meal blood sugar measurement regression linear equation and storing the calculated first pre-meal blood sugar measurement regression linear equation in a DB for a first pre-meal blood sugar regression linear equation in the method of measuring robust continuous blood sugar using a skin image according to the embodiment of the present disclosure, and FIG. 6 is a diagram illustrating the first pre-meal blood sugar regression linear equation.

In step S301, the apparatus for measuring blood sugar captures a skin image using a camera of a smart device and detects a skin ROI.

In step S302, the apparatus for measuring blood sugar converts the RGB color system designated as one of various color systems in the detected skin ROI into the $YC_gC_o$ and $YC_bC_r$ color systems to calculate $C_r$ and $C_o$, and stores the average value of the $C_rC_o$ color data, to which the weighted average is applied, in the "color data DB."

In step S303, the apparatus for measuring blood sugar stores pre-meal blood sugar data measured using a blood sugar meter in the "pre-meal blood sugar DB."

In step S304, the apparatus for measuring blood sugar applies the regression analysis to the color data DB of the skin image and the pre-meal blood sugar DB that stores the pre-meal blood sugar data measured using the blood sugar meter to calculate the first pre-meal blood sugar regression linear equation, and stores the calculated first pre-meal blood sugar regression linear equation in the "first pre-meal blood sugar regression linear equation DB." The first pre-meal blood sugar regression linear equation for the estimated blood sugar and the actual blood sugar is illustrated in FIG. 6.

Figure 7:
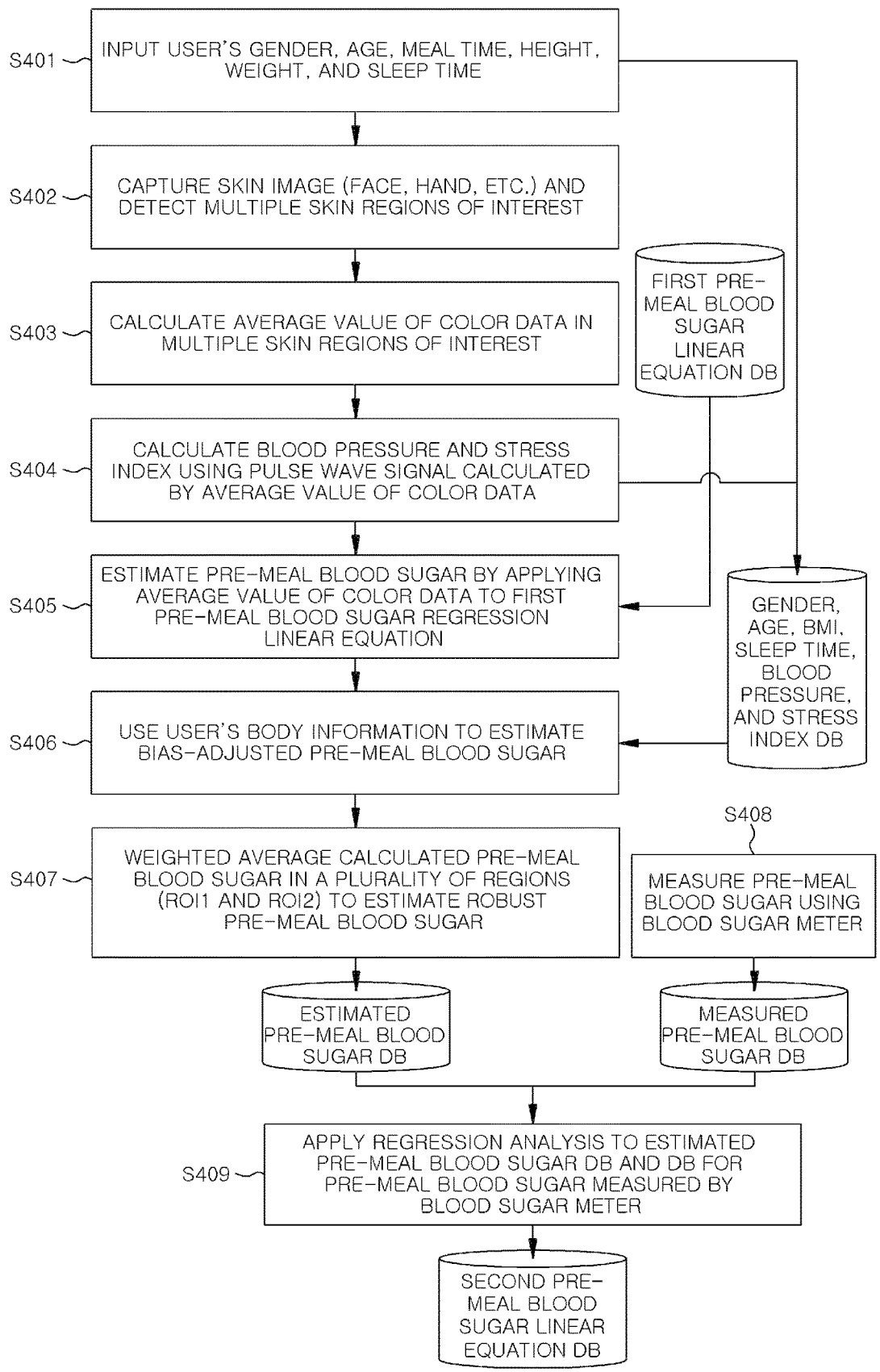
FIG. 7 is a flowchart illustrating a process of calculating a second pre-meal blood sugar measurement regression linear equation and storing the calculated second pre-meal blood sugar measurement regression linear equation in a database (DB) for a second pre-meal blood sugar regression linear equation in the method of measuring robust continuous blood sugar using a skin image according to the embodiment of the present disclosure.

FIG. 7 is a flowchart illustrating a process of calculating a second pre-meal blood sugar measurement regression linear equation and storing the calculated second pre-meal blood sugar measurement regression linear equation in a DB for a second pre-meal blood sugar regression linear equation in the method of measuring robust continuous blood sugar using a skin image according to the embodiment of the present disclosure.

In step S401, the apparatus for measuring blood sugar according to an embodiment of the present disclosure receives a user's gender, age, meal time, height, weight, and sleep time from a user.

In step S402, the apparatus for measuring blood sugar captures a skin image using a camera of a smart device, and detects the skin ROI (ROI1, ROI2, etc.).

In step S403, the apparatus for measuring blood sugar converts the RGB color system designated as one of the various color systems in the detected skin ROI into the $YC_gC_o$ and $YC_bC_r$ color systems to calculate $C_r$ and $C_o$ and calculate the average value of the $C_rC_o$ color data to which the weighted average is applied.

In step S404, the apparatus for measuring blood sugar calculates a blood pressure and a stress index using a pulse wave signal calculated through the average value of the color data. Here, the input user's gender, age, height, weight, and sleep time, and the calculated blood pressure and stress index are stored in the DB for the user' gender, age, BMI, sleep time, blood pressure, and stress index.

In step S404, the apparatus for measuring blood sugar applies the average value of the $C_rC_o$ color data to which the weighted average is applied to the "first pre-meal blood sugar regression linear equation DB" to estimate the pre-meal blood sugar.

In step S406, the apparatus for measuring blood sugar estimates bias-adjusted pre-meal blood sugar using the user's body information (gender, age, BMI, sleep time, blood pressure, and stress index).

In step S407, the apparatus for measuring blood sugar stores the robust pre-meal blood sugar estimated by weighted averaging of the pre-meal blood sugar estimated at multiple regions at all times/continuously in the "estimated pre-meal blood sugar DB."

In step S408, the apparatus for measuring blood sugar stores the pre-meal blood sugar data measured using the blood sugar meter in the "pre-meal blood sugar DB."

In step S409, the apparatus for measuring blood sugar applies the regression analysis to the pre-meal blood sugar DB that stores the pre-meal blood sugar data estimated based on the skin image and the pre-meal blood sugar DB that stores the pre-meal blood sugar data measured using the blood sugar meter to calculate the second pre-meal blood sugar regression linear equation and store the calculated second pre-meal blood sugar regression linear equation in the "second pre-meal blood sugar regression linear equation DB."

Figure 8:
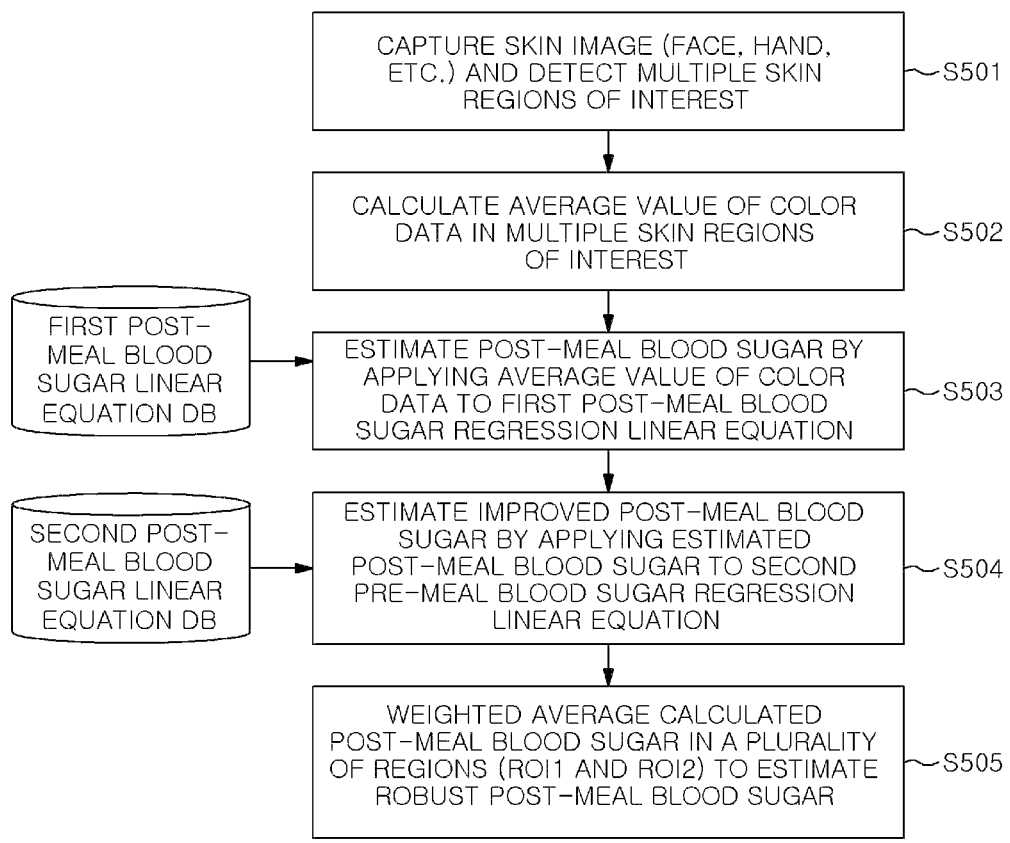
FIG. 8 is a flowchart illustrating a process of estimating post-meal blood sugar using a skin image in the method of measuring robust continuous blood sugar using a skin image according to the embodiment of the present disclosure.

FIG. 8 is a flowchart illustrating a process of estimating post-meal blood sugar using a skin image in the method of measuring robust continuous blood sugar using a skin image according to the embodiment of the present disclosure.

In step S501, the apparatus for measuring blood sugar captures a skin image using a camera of a smart device and detects multiple skin ROIs (ROI1, ROI2, etc.).

In step S502, the apparatus for measuring blood sugar converts the RGB color system designated as one of the various color systems in the detected skin ROI into the $YC_gC_o$ and $YC_bC_r$ color systems to calculate $C_r$ and $C_o$ and calculate the average value of the $C_rC_o$ color data to which the weighted average is applied.

In step S503, the apparatus for measuring blood sugar estimates the post-meal blood sugar by applying the average value of the $C_rC_o$ color data to which the weighted average is applied to the "first post-meal blood sugar regression linear equation."

In step S504, the apparatus for measuring blood sugar applies the estimated post-meal blood sugar to the "second post-meal blood sugar regression linear equation" to estimate improved post-meal blood sugar.

In step S505, the apparatus for measuring blood sugar may measure the robust post-meal blood sugar by weighted averaging of the post-meal blood sugar estimated at multiple regions at all times/continuously.

Figure 9:
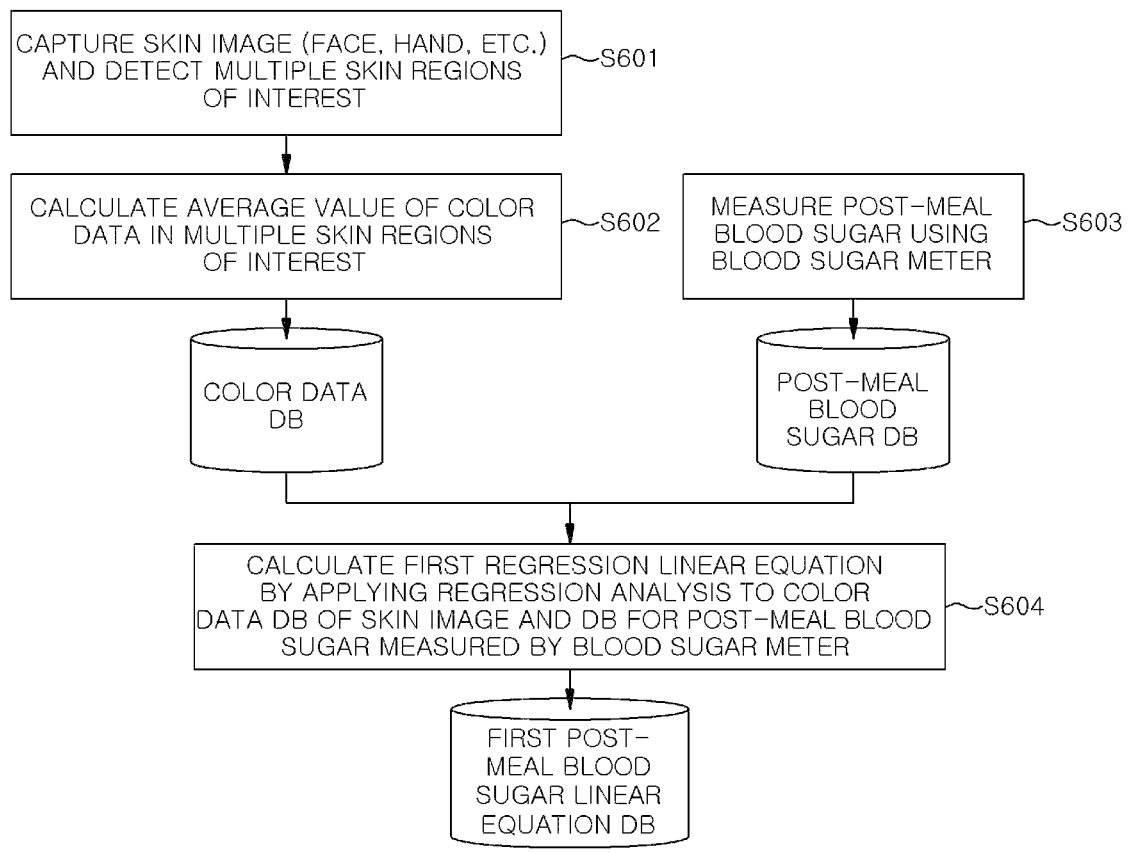
FIG. 9 is a flowchart illustrating a process of calculating a first post-meal blood sugar measurement regression linear equation and storing the calculated first post-meal blood sugar measurement regression linear equation in a database (DB) for a first post-meal blood sugar regression linear equation in the method of measuring robust continuous blood sugar using a skin image according to the embodiment of the present disclosure.
Figure 10:
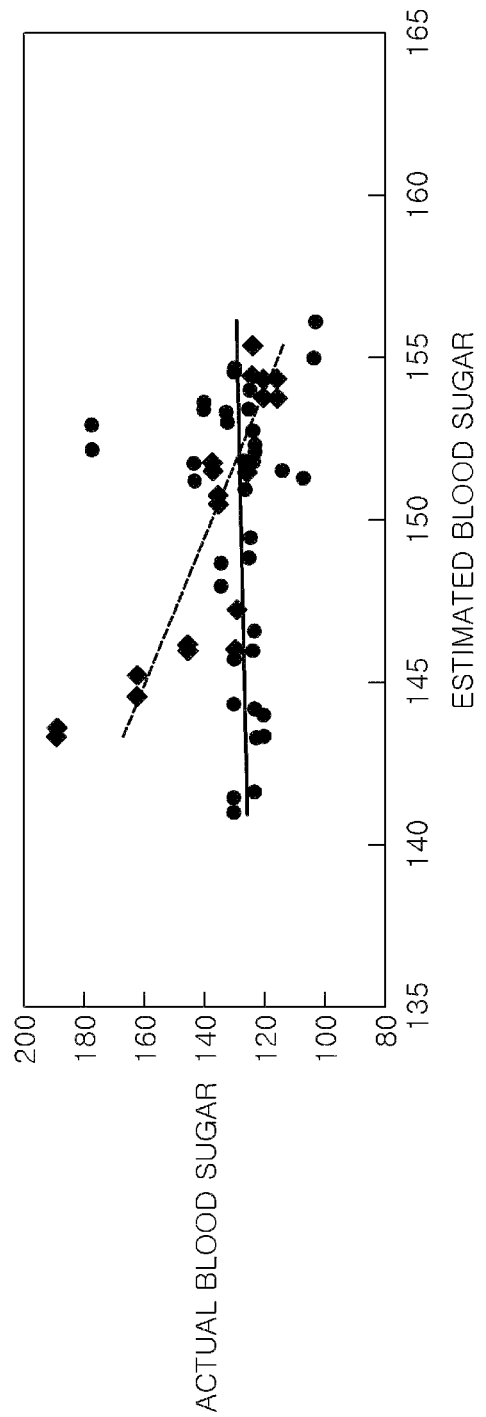
FIG. 10 is a diagram illustrating the first pre-meal blood sugar regression linear equation.

FIG. 9 is a flowchart illustrating a process of calculating a first post-meal blood sugar measurement regression linear equation and storing the calculated first post-meal blood sugar measurement regression linear equation in a DB for a first post-meal blood sugar regression linear equation in the method of measuring robust continuous blood sugar using a skin image according to the embodiment of the present disclosure, and FIG. 10 is a diagram illustrating the first post-meal blood sugar regression linear equation.

In step S601, the apparatus for measuring blood sugar captures a skin image using a camera of a smart device and detects a skin ROI.

In step S602, the apparatus for measuring blood sugar converts the RGB color system designated as one of various color systems in the detected skin ROI into the $YC_gC_o$ and $YC_bC_r$ color systems to calculate $C_r$ and $C_o$, and stores the average value of the $C_rC_o$ color data to which the weighted average is applied in the "color data DB."

In step S603, the apparatus for measuring blood sugar stores the post-meal blood sugar data measured using a blood sugar meter in the "post-meal blood sugar DB."

In step S604, the apparatus for measuring blood sugar applies the regression analysis to "the color data DB" of the skin image and the "post-meal blood sugar DB" that stores the post-meal blood sugar data measured using the blood sugar meter to calculate the first post-meal blood sugar regression linear equation, and stores the calculated first post-meal blood sugar regression linear equation in the "first post-meal blood sugar regression linear equation DB." The first post-meal blood sugar regression linear equation for the estimated blood sugar and the actual blood sugar is illustrated in FIG. 10.

Figure 11:
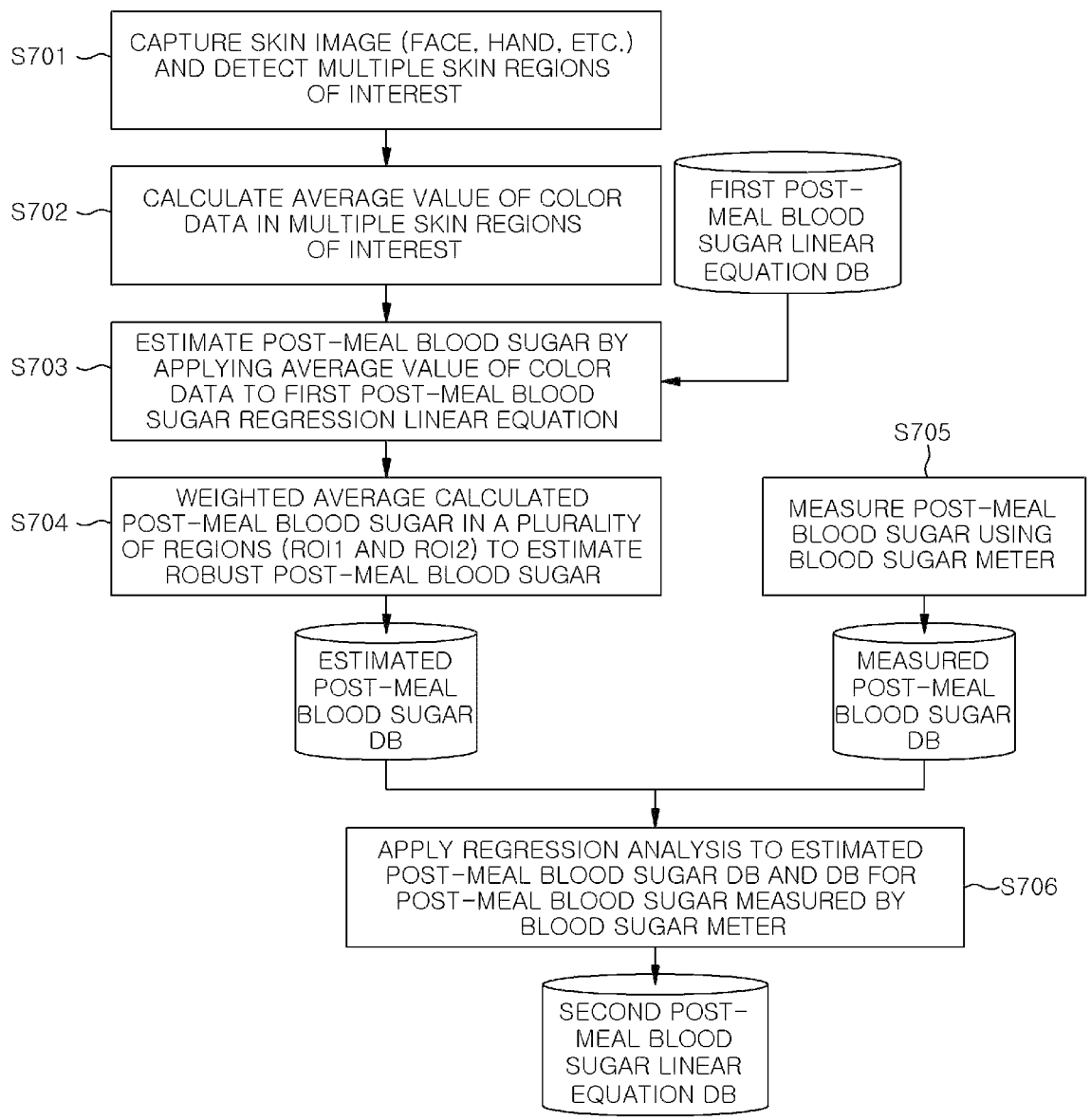
FIG. 11 is a flowchart illustrating a process of calculating a second post-meal blood sugar measurement regression linear equation and storing the calculated second post-meal blood sugar measurement regression linear equation in a database (DB) for a second post-meal blood sugar regression linear equation in the method of measuring robust continuous blood sugar using a skin image according to the embodiment of the present disclosure.

FIG. 11 is a flowchart illustrating a process of calculating a second post-meal blood sugar measurement regression linear equation and storing the calculated second post-meal blood sugar measurement regression linear equation in the DB for the second post-meal blood sugar regression linear equation in the method of measuring robust continuous blood sugar using a skin image according to the embodiment of the present disclosure.

In step S701, the apparatus for measuring blood sugar according to the embodiment of the present disclosure captures a skin image using a camera of a smart device and detects the skin ROI ($ROI_1$, $ROI_2$, etc.).

In step S702, the apparatus for measuring blood sugar converts the RGB color system designated as one of the various color systems in the detected skin ROI into the $YC_gC_o$ and $YC_bC_r$ color systems to calculate $C_r$ and $C_o$ and calculate the average value of the $C_rC_o$ color data to which the weighted average is applied.

In step S703, the apparatus for measuring blood sugar estimates the post-meal blood sugar by applying the average value of the $C_rC_o$ color data to which the weighted average is applied to the "first post-meal blood sugar regression linear equation DB."

In step S704, the apparatus for measuring blood sugar stores, in the "estimated post-meal blood sugar DB," the robust blood sugar estimated by weighted averaging of the estimated post-meal blood sugar at multiple regions at all times/continuously.

In step S705, the apparatus for measuring blood sugar stores the post-meal blood sugar data measured using a blood sugar meter in the "post-meal blood sugar DB."

In step S706, the apparatus for measuring blood sugar applies the regression analysis to the post-meal blood sugar DB that stores the post-meal blood sugar data estimated based on the skin image and the post-meal blood sugar DB that stores the post-meal blood sugar data measured using the blood sugar meter to calculate the second post-meal blood sugar regression linear equation and store the calculated second post-meal blood sugar regression linear equation in the "second post-meal blood sugar regression linear equation DB."

Meanwhile, in a method of interpreting a theoretical dependence relationship between variables, the relationship between two variables is represented by a straight line obtained by representing a set of points on a scatter diagram as a straight line, and in an embodiment of the present disclosure, the first and second regression linear equations are estimated using the relationship between two variables.

First, according to the embodiment of the present disclosure, the regression analysis is applied to an "actual blood sugar DB" that stores the actual blood sugar data collected through a blood sugar measuring instrument and a "color data average value DB" that stores the color data average values extracted from a face image captured using a camera of a smart device, and the estimated regression analysis is stored in the first regression analysis equation DB.

Second, according to the embodiment of the present disclosure, the regression analysis is applied to the "estimated blood sugar DB" that stores fasting blood sugar data bias-adjusted based on user information (gender, age, meal time, height, weight, and sleeping time) and "standard fasting blood sugar information by gender and age of, for example, Koreans" and the "actual blood sugar DB" to calculate the regression linear equation. The calculated regression linear equation is stored in the second regression analysis equation DB. The regression linear equation is as shown in equation 1 below:

<Equation 1>

$$y = ax + b$$

In the calculation of the first regression linear equation, an x value denotes an average value of the selected color system (in the present disclosure, average data of $C_r$ color data is used), and a y value denotes the "actual blood sugar" measured from the blood sugar measuring instrument.

In calculating the second regression linear equation, the x value denotes the "estimated blood sugar," and the y value denotes the "improved blood sugar."

In table 1, x denotes the average value of the color data of the region of interest in the face image of the selected color system (in an embodiment of the present disclosure, $C_r$ is used) and is applied to the blood sugar regression linear equation to calculate y (estimated blood sugar). For the regression linear expression calculation result before and after each meal time obtained by applying the actual data, constant a and b values may change according to the color data of the skin ROI used and the blood sugar data measured.

The blood sugar regression linear equation calculated by applying the regression analysis to the "color data average value DB" and the "actual blood sugar DB" is as shown in table 1 below. Table 1 below shows the "blood sugar regression linear equation" estimated through the "$C_r$ color data average DB" and the "actual blood sugar DB."

TABLE 1

| Male | Before breakfast | y = −0.1809x + 126.6260 |
|---|---|---|
| | After breakfast | y = −0.9496x + 272.2469 |
| | Before lunch | y = 0.4598x + 35.4234 |
| | After lunch | y = 0.2187x + 95.0316 |
| | Before dinner | y = −0.0063x + 105.8861 |
| | After dinner | y = 5460x + 50.0310 |
| Female | Before breakfast | y = −1.1453x + 266.2432 |
| | After breakfast | y = −1.6961x + 379.6073 |
| | Before lunch | y = −1.9175x + 390.0815 |
| | After lunch | y = −4.4413x + 803.5027 |
| | Before dinner | y = −2.6370x + 786.8008 |
| | After dinner | y = −2.9235x + 569.2966 |

In table 2, x is the blood sugar estimated from the face image, and y (improved blood sugar) is calculated by applying the estimated blood sugar to the improved blood sugar regression linear equation. For the regression linear expression calculation result before and after each meal time obtained by applying the actual data, constant a and b values may change according to the color data of the skin ROI used and the blood sugar data measured.

The improved blood sugar regression linear equation calculated by applying the regression analysis to the "estimated blood sugar DB" and the "actual blood sugar DB" is as shown in table 2 below. Table 2 shows the "improved blood sugar regression linear equation" estimated through the "estimated blood sugar DB" and the "actual blood sugar DB."

TABLE 2

| Male | Before breakfast | y = 1.0000x + 0.0036 |
|---|---|---|
| | After breakfast | y = 1.0000x − 0.0033 |
| | Before lunch | y = 1.0001x − 0.0038 |
| | After lunch | y = 1.0000x + 0.0040 |
| | Before dinner | y = 0.9941x + 0.6262 |
| | After dinner | y = 0.9999x + 0.0026 |
| Female | Before breakfast | y = 1.0000x − 0.0062 |
| | After breakfast | y = 1.0000x − 0.0031 |
| | Before lunch | y = 1.0000x − 0.0053 |
| | After lunch | y = 1.0000x − 0.0037 |
| | Before dinner | y = 1.0000x + 0.0018 |
| | After dinner | y = 1.0000x + 0.0023 |

According to an embodiment of the present disclosure, the extracted $C_r$ color data value may be applied to the first regression analysis equation DB to calculate the estimated blood sugar in the designated region of interest of the face image, and the estimated value may be applied to the second regression analysis equation DB to measure the improved blood sugar.

Figure 12:
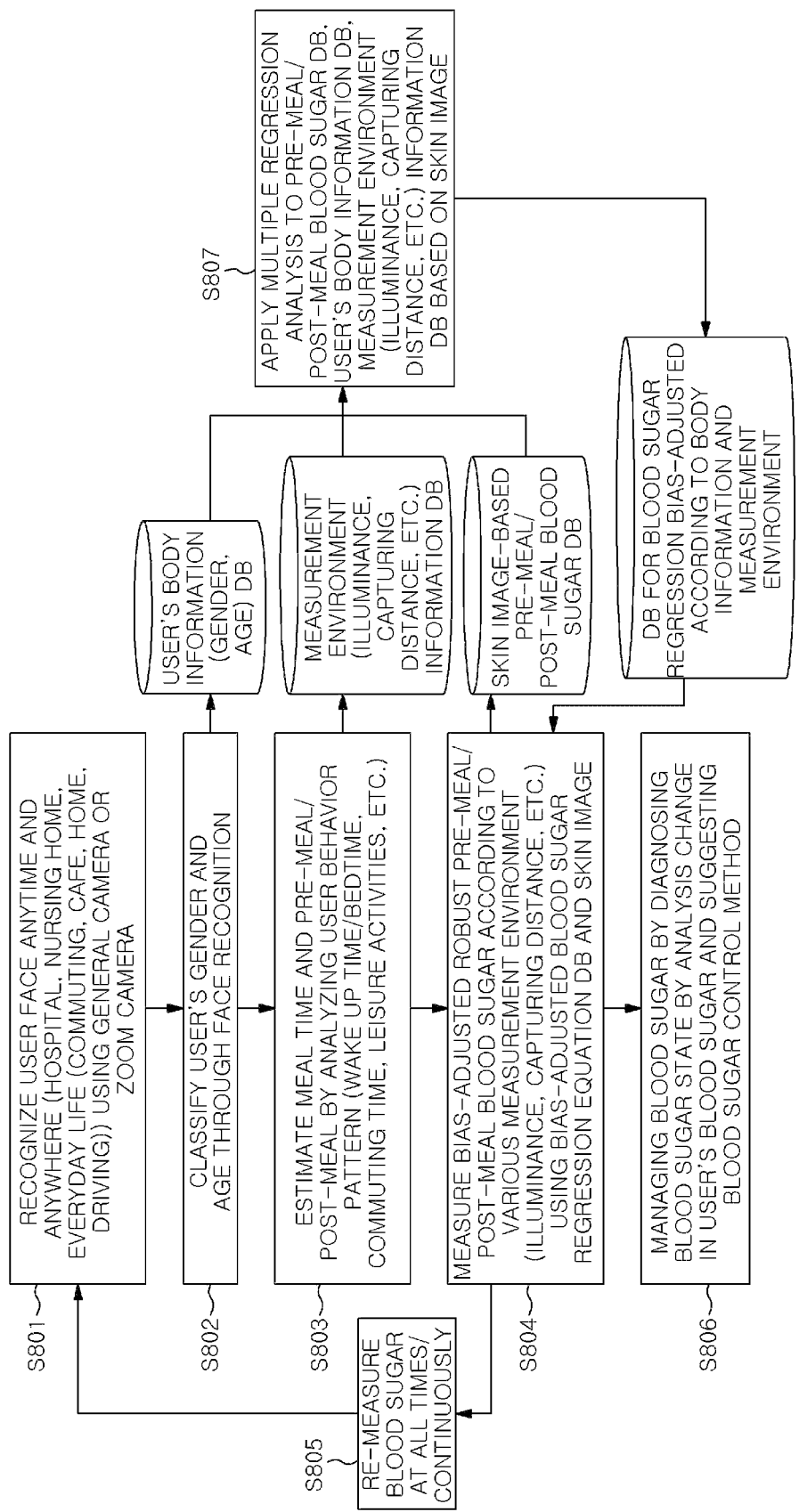
FIG. 12 is a diagram illustrating a process of measuring bias-adjusted robust pre-meal/post-meal blood sugar according to user's body information and a measurement environment by using the skin image anytime and anywhere in the method of measuring robust continuous blood sugar using a skin image according to the embodiment of the present disclosure.

FIG. 12 is a diagram illustrating a process of measuring bias-adjusted robust pre-meal/post-meal blood sugar according to a user's body information and measurement environment by using the skin image anytime and anywhere in the method of measuring robust continuous blood sugar using a skin image according to the embodiment of the present disclosure.

In steps S801 and S802, the apparatus for measuring blood sugar according to the embodiment of the present disclosure is used anytime and anywhere (hospital, nursing home, commuting, cafe, home, driving in a vehicle, etc.) using a general camera, a zoom camera, a wearable device, or the like to recognize a user's face and classify a user's gender and age.

In addition, in step S803, the apparatus for measuring blood sugar estimates meal time by analyzing user behavior patterns (wake up time/bedtime, commuting time, leisure activities, etc.) and classifies pre-meal/post-meal based on the estimated meal time.

In step S804, the apparatus for measuring blood sugar measures the robust pre-meal/post-meal blood sugar bias-adjusted according to the measurement environment (illuminance, capturing distance, etc.) at all times/continuously by using the pre-constructed "blood sugar regression equation DB that stores the blood sugar regression equation data bias-adjusted according to body information and environment" and the skin image.

In step S805, the apparatus for measuring blood sugar may re-measure the pre-meal/post-meal blood sugar at all times/continuously.

In addition, in step S806, the apparatus for measuring blood sugar may be managed by suggesting a method of diagnosing a blood sugar state and controlling blood sugar based on the change in user's blood sugar analyzed through monitoring.

Meanwhile, in step S807, the apparatus for measuring blood sugar applies multiple regression analysis to the "pre-meal/post-meal blood sugar DB that stores pre-meal/post-meal blood sugar data measured using skin images," the "user body information (gender, age) DB," and the "measurement environment information DB" based on the pre-recorded user behavior patterns, the blood sugar measured based on the skin image, and the measurement environment log data to calculate the multiple regression equations, and stores the calculated multiple regression equations in the "blood sugar regression equation DB that stores the blood sugar regression equation data bias-adjusted according to the body information and the measurement environment." As such, the "blood sugar regression equation DB that stores the blood sugar regression equation data bias-adjusted according to the body information and the measurement environment" is constructed in advance and used in step S804.

Meanwhile, the robust pre-meal/post-meal blood sugar measurement using the skin image anytime and anywhere may be taken not only by a general camera, an infrared camera, and a zoom camera, but also by cameras of infrared light of wearable devices (wristwatch type, body (ear, face, etc.) attachment type, etc.). As an example, the apparatus for measuring blood sugar detects a skin ROI of a hand image captured by infrared light of a wristwatch-type wearable device. The apparatus for measuring blood sugar applies the color data calculated in the detected skin ROI to the "first pre-meal blood sugar regression linear equation" when the user's blood sugar measurement time is pre-meal to estimate the initial pre-meal (breakfast, lunch, and dinner) blood sugar, uses the user's body information (gender, age, BMI, sleep time, blood pressure, and stress index) to estimate the bias-adjusted pre-meal blood sugar, and applies the estimated pre-meal blood sugar (bias-adjusted pre-meal blood sugar) to the "second pre-meal blood sugar regression linear equation" to estimate the improved pre-meal blood sugar. The apparatus for measuring blood sugar applies the color data to the "first post-meal blood sugar regression linear equation" when the user's blood sugar measurement time is post-meal to estimate the post-meal (breakfast, lunch, and dinner) blood sugar, and applies the estimated post-meal blood sugar to the "second post-meal blood sugar regressive linear equation" to estimate the improved post-meal blood sugar.

Figure 13:
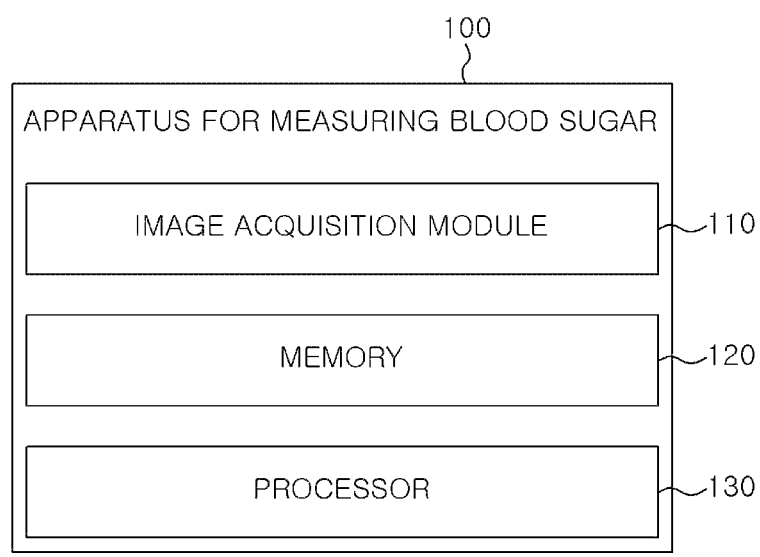
FIG. 13 is a configuration diagram for describing a configuration of an apparatus for measuring robust continuous blood sugar using a skin image according to an embodiment of the present disclosure.

FIG. 13 is a configuration diagram for describing a configuration of an apparatus for measuring robust continuous blood sugar using a skin image according to an embodiment of the present disclosure.

As illustrated in FIG. 13, an apparatus 100 for measuring blood sugar according to an embodiment of the present disclosure includes an image acquisition module 110, a memory 120, and a processor 130. However, all of the illustrated components are not essential components. The apparatus 100 for measuring blood sugar may be implemented using more components than the illustrated components, and the apparatus 100 for measuring blood sugar may be implemented by fewer components than that.

Hereinafter, a detailed configuration and operation of each component of the apparatus 100 for measuring blood sugar of FIG. 13 will be described.

The image acquisition module 110 acquires a skin image captured by not only a general camera, an infrared camera, and a zoom camera, but also a camera or the like of infrared light or the like of a wearable device (a wrist watch type, a body (ear, face, etc.) attachment type, etc.). The skin image includes multiple skin ROIs.

The memory 120 stores one or more programs. The memory 120 includes a user meal time DB, a first pre-meal blood sugar regression linear equation DB, a DB for a user's gender, age, BMI, sleep time, blood pressure, and stress index, a second pre-meal blood sugar regression linear equation DB, a first post-meal blood sugar regression linear equation DB, a second post-meal blood sugar regression linear equation DB, a color data DB, a pre-meal blood sugar DB, an estimated pre-meal blood sugar DB, a measured pre-meal blood sugar DB, a post-meal blood sugar DB, an estimated post-meal blood sugar DB, and a measured post-meal blood sugar DB.

The processor 130 is configured to execute the one or more programs stored in the memory 120. Further, the processor 130 calculates color data from the multiple skin regions of interest in the acquired skin image, classifies a user's meal state into a pre-meal state or a post-meal state through analysis of acquired user information, estimates blood sugar by applying the calculated color data to a blood sugar regression linear equation corresponding to the classified user's meal state, and weighted averages the estimated blood sugar to measure robust blood sugar.

According to the embodiments, the processor 130 may diagnose a blood sugar state by analyzing a change in user's blood sugar.

According to the embodiments, the processor 130 may provide a blood sugar control method according to the diagnosed blood sugar state.

According to the embodiments, the processor 130 may calculate a blood pressure and a stress index using a pulse wave signal calculated through the calculated color data.

According to the embodiments, the acquired user information may include meal time and at least one of gender, age, height, weight, and sleep time.

According to the embodiments, the processor 130 may estimate first pre-meal blood sugar by applying the calculated color data to a first pre-meal blood sugar regression linear equation.

According to the embodiments, the processor 130 may estimate bias-adjusted second pre-meal blood sugar by bias-adjusting the estimated first pre-meal blood sugar using the acquired user information.

According to the embodiments, the processor 130 may apply the estimated second pre-meal blood sugar to a second pre-meal blood sugar regression linear equation to estimate third pre-meal blood sugar.

According to the embodiments, the processor 130 may estimate first post-meal blood sugar by applying the calculated color data to a first post-meal blood sugar regression linear equation.

According to the embodiments, the processor 130 may estimate bias-adjusted second post-meal blood sugar by bias-adjusting the estimated first post-meal blood sugar using the acquired user information.

According to the embodiments, the processor 130 may apply the estimated second post-meal blood sugar to a second post-meal blood sugar regression linear equation to estimate third post-meal blood sugar.

According to the embodiments, the processor 130 may calculate a multiple regression equation by applying multiple regression analysis to pre-meal/post-meal blood sugar based on the skin image, user's body information, and measurement environment information to obtain a multiple regression equation based on a user behavior pattern, blood sugar measured based on the skin image, and measurement environment log data, and construct a blood sugar regression equation DB that stores the blood sugar regression equation data bias-adjusted according to the user's body information and the measurement environment information using the calculated multiple regression equation.

According to the embodiments, the processor 130 may confirm the user's body information through image recognition, estimate a meal time by analyzing the user behavior pattern and classifies the user's meal state into the pre-meal state or the post-meal state based on the estimated meal time, and measure the robust blood sugar bias-adjusted according to the measurement environment information using the blood sugar regression equation, which is bias-adjusted according to the user's body information and the measurement environment information, and the skin image.

Meanwhile, a blood sugar measurement experiment using a face image and experimental results will be reviewed.

In order to confirm the performance of the method of measuring blood sugar using the face image, an experiment was conducted using a camera of a smart device.

The time and location were identically set using the camera of the smart device, and the face image was captured, and at the same time, the blood sugar was measured. In the present disclosure, an average value of $C_r$ color data extracted by converting an RGB color system to a $YC_bC_r$ color system was used as an example of one of the color systems.

In the experiment, the blood sugar was measured a total of 6 times per person before and after breakfast, before and after lunch, and before and after dinner, and the face image was captured a total of 12 times per person for 10 seconds before and after blood collection each time that blood was collected for blood sugar measurement. A total of 180 experiments (30 subjects each) were performed to estimate the blood sugar regression linear using the Cr color data average value DB in the region of interest of the face image and the actual blood sugar DB that stores the actual blood sugar data collected through the blood sugar measuring instrument, and the average value of the $C_r$ color data calculated from the face image was applied to the blood sugar regression linear to calculate the accuracy. Table 3 shows blood sugar estimation accuracy results (application of first regression analysis).

TABLE 3

| | Division | Error rate | Absolute error |
|---|---|---|---|
| Male | Before breakfast | 5.1151% | 4.9385 |
| | After breakfast | 10.3687% | 14.0003 |
| | Before lunch | 8.2038% | 8.6263 |
| | After lunch | 7.1752% | 9.3373 |
| | Before dinner | 6.6824% | 6.9487 |
| | After dinner | 10.3125% | 13.5402 |
| Female | Before breakfast | 5.2429% | 4.9143 |
| | After breakfast | 14.3698% | 17.0759 |
| | Before lunch | 9.2599% | 9.1230 |
| | After lunch | 5.8080% | 8.3117 |
| | Before dinner | 6.0841% | 6.0606 |
| | After dinner | 12.2165% | 16.9246 |

The measurement results of accuracy of blood sugar estimated by applying the average value of the Cr color data of the face image to the blood sugar regression linear equation was obtained as shown in Table 3 for each gender and meal time, and the accuracy results calculated by applying the estimated blood sugar calculated from the blood sugar regression linear equation to the improved blood sugar regression linear equation is shown in table 4 below.

TABLE 4

| | Division | Error rate | Absolute error |
|---|---|---|---|
| Male | Before breakfast | 5.1142% | 4.9374 |
| | After breakfast | 10.3679% | 13.9995 |
| | Before lunch | 8.2037% | 8.6257 |
| | After lunch | 7.1761% | 9.3381 |
| | Before dinner | 6.6829% | 6.9487 |
| | After dinner | 10.3109% | 13.5392 |
| Female | Before breakfast | 5.2438% | 4.9156 |
| | After breakfast | 14.3697% | 17.0356 |
| | Before lunch | 9.2604% | 9.1241 |
| | After lunch | 5.8078% | 8.3117 |
| | Before dinner | 6.0846% | 6.0610 |
| | After dinner | 12.2171% | 16.9251 |

When the second regression linear equation was used, it was confirmed that the error rate was lower than when the first regression linear equation was applied.

According to an embodiment of the present disclosure, in measuring blood sugar from a face image, a skin image may be captured from a smart device owned by a user without a separate hardware module, and blood sugar may be estimated from a skin ROI, and the estimated value may be used to measure the improved blood sugar.

This may be used to provide a fast and convenient blood sugar system for general users anytime and anywhere. In addition, it is possible to effectively replace the blood sugar measuring instrument of the invasive and blood collection method commonly used in relation to the situation requiring the blood sugar management.

Meanwhile, there may be provided a non-transitory computer-readable storage medium storing computer-executable instructions which cause, when executed by a processor, the processor to perform a method that includes: calculating color data from multiple skin regions of interest in the skin image; classifying a user's meal state into a pre-meal state or a post-meal state through analysis of acquired user information; estimating blood sugar by applying the calculated color data to a blood sugar regression linear equation corresponding to the classified user's meal state; and weighted averaging the estimated blood sugar to measure robust blood sugar.

Further, according to an embodiment of the present disclosure, the various embodiments described above may be implemented as software including instructions stored in a machine-readable storage media. The machine (e.g., a computer) may be a device capable of calling a stored instruction from a storage medium and operating according to the called instruction, and may include an electronic device according to the disclosed embodiments. When the instruction is executed by the processor, the processor may perform a function corresponding to the instruction directly or by using other components under the control of the processor. The instruction may include a code generated or executed by a compiler or an interpreter. The machine-readable storage media may be provided in a form of a non-transitory storage medium. Herein, the 'non-transitory' indicates that the storage medium does not include a signal and is tangible, but does not distinguish that the data is stored in the storage medium semi-permanently or temporarily.

In addition, according to an embodiment of the present disclosure, a method according to various embodiments described above may be provided by being included in a computer program product. The computer program product may be traded between a seller and a buyer as a commodity. The computer program product may be distributed in a form of the machine-readable storage media (e.g., compact disc read only memory (CD-ROM)) or through an application store (e.g., Play Store™) by online. In the case of online distribution, at least part of the computer program product may be temporarily stored or temporarily generated in a storage medium such as a server of a manufacturer, a server of an application store, or a memory of a relay server.

Further, according to an embodiment of the present disclosure, the various embodiments described above may be implemented in a medium that may be read by a computer or a similar device by using software, hardware, or a combination thereof. In some cases, the embodiments described in this application may be implemented by the processor itself. According to software implementation, embodiments such as procedures and functions described in this application may be implemented by separate software modules. Each of the software modules may perform one or more functions and operations described in this application.

Meanwhile, computer instructions for performing a processing operation of a device according to the various embodiments described above may be stored in a non-transitory computer-readable medium. When the computer instructions stored in the non-transitory computer-readable medium are executed by the processor of the specific device, the computer instructions cause the specific device to perform processing operations according to the various embodiments described above. The non-transitory computer-readable medium refers to a medium that stores data semi-permanently rather than a medium such as registers, caches, and memory that stores data for a short moment, and may be read by a device. Specific examples of the non-transitory computer-readable media may include CD, DVD, hard disk, Blu-ray disk, USB, memory card, ROM, and the like.

In addition, each of the components (e.g., a module or a program) according to the various embodiments described above may include a singular or plural entity, and a part of the above-described sub-components may be omitted, or another sub-component may be further included in the various embodiments. Alternatively or additionally, a part of components (e.g., the module or the program) may be integrated into a single entity, thereby identically or similarly performing functions performed by each of the components before the integration. The operations performed by the module, the program, or another component according to various embodiments may be executed sequentially, parallel, repetitively, or heuristically, at least a part of operations may be executed in a different order or omitted, or another operation may be added.

While certain embodiments have been described, these embodiments have been presented by way of example only and are not intended to limit the scope of the disclosures. Indeed, the embodiments described herein may be embodied in a variety of other forms. Furthermore, various omissions, substitutions and changes in the form of the embodiments described herein may be made departing from the spirit of the disclosures. The accompanying claims and their equivalents are intended to cover such forms or modifications as would fall within the scope and spirit of the disclosures.

What is claimed is:

1. A method for measuring blood sugar using an apparatus for measuring blood, the method comprising:
   calculating color data from multiple skin regions of interest in a skin image;
   classifying a user's meal state into a pre-meal state or a post-meal state through analysis of acquired user information;
   estimating blood sugar by applying the calculated color data to a blood sugar regression linear equation corresponding to the classified user's meal state; and
   measuring robust blood sugar by weighted averaging the estimated blood sugar.

2. The method of claim 1, further comprising:
   diagnosing a blood sugar state by analyzing a change in the estimated blood sugar.

3. The method of claim 2, further comprising:
   providing a blood sugar control method according to the diagnosed blood sugar state.

4. The method of claim 1, further comprising:
   calculating a blood pressure and a stress index using a pulse wave signal calculated through the calculated color data.

5. The method of claim 1, wherein the acquired user information includes meal time and at least one of gender, age, height, weight, and sleep time.

6. The method of claim 1, wherein the estimating of the blood sugar includes applying the calculated color data to a first pre-meal blood sugar regression linear equation to estimate first pre-meal blood sugar.

7. The method of claim 6, wherein the estimating of the blood sugar includes bias-adjusting the estimated first pre-meal blood sugar using the acquired user information to estimate bias-adjusted second pre-meal blood sugar.

8. The method of claim 7, wherein the estimating of the blood sugar includes applying the estimated bias-adjusted second pre-meal blood sugar to a second pre-meal blood sugar regression linear equation to estimate third pre-meal blood sugar.

9. The method of claim 1, wherein the estimating of the blood sugar includes applying the calculated color data to a first post-meal blood sugar regression linear equation to estimate first post-meal blood sugar.

10. The method of claim 9, wherein the estimating of the blood sugar includes bias-adjusting the estimated first post-meal blood sugar using the acquired user information to estimate bias-adjusted second post-meal blood sugar.

11. The method of claim 10, wherein the estimating of the blood sugar includes applying the estimated bias-adjusted second post-meal blood sugar to a second post-meal blood sugar regression linear equation to estimate third post-meal blood sugar.

12. The method of claim 1, further comprising:
   calculating a multiple regression equation by applying multiple regression analysis to estimate pre-meal/post-meal blood sugar based on the estimated blood sugar calculated from the skin image, user's body information, and measurement environment information to obtain the calculated multiple regression equation based on a user behavior pattern, the estimated blood sugar measured based on the skin image, and measurement environment log data; and
   constructing a blood sugar regression equation database that stores blood sugar regression equation data bias-adjusted according to the user's body information and the measurement environment information using the calculated multiple regression equation.

13. The method of claim 12, further comprising:
   confirming the user's body information through image recognition;
   estimating a meal time by analyzing the user behavior pattern, and classifying the user's meal state into a pre-meal state or a post-meal state based on the estimated meal time; and measuring the robust blood sugar bias-adjusted according to the measurement environment information using the blood sugar regression equation, which is bias-adjusted according to the user's body information and the measurement environment information, and the skin image.

14. An apparatus for measuring robust continuous blood sugar using a skin image, the apparatus comprising:
a camera to acquire the skin image including multiple skin regions of interest;
a memory configured to store one or more programs; and
a processor configured to execute the stored one or more programs,
wherein the processor
calculates color data from the multiple skin regions of interest in the acquired skin image,
classifies a user's meal state into a pre-meal state or a post-meal state through analysis of acquired user information, and
estimates blood sugar by applying the calculated color data to a blood sugar regression linear equation corresponding to the classified user's meal state, and weighted averages the estimated blood sugar to measure robust blood sugar.

15. The apparatus of claim 14, wherein the processor diagnoses a blood sugar state by analyzing a change in estimated blood sugar.

16. The apparatus of claim 15, wherein the processor provides a blood sugar control method according to the diagnosed blood sugar state.

17. The apparatus of claim 14, wherein the processor estimates first pre-meal blood sugar by applying the calculated color data to a first pre-meal blood sugar regression linear equation,
estimates bias-adjusted second pre-meal blood sugar by bias-adjusting the estimated first pre-meal blood sugar using the acquired user information, and
applies the estimated bias-adjusted second pre-meal blood sugar to a second pre-meal blood sugar regression linear equation to estimate third pre-meal blood sugar.

18. The apparatus of claim 14, wherein the processor estimates first post-meal blood sugar by applying the calculated color data to a first post-meal blood sugar regression linear equation,
estimates bias-adjusted second post-meal blood sugar by bias-adjusting the estimated first post-meal blood sugar using the acquired user information, and
applies the estimated bias-adjusted second post-meal blood sugar to a second post-meal blood sugar regression linear equation to estimate third post-meal blood sugar.

19. The apparatus of claim 14, wherein the processor is configured to:
calculate a multiple regression equation by applying multiple regression analysis to pre-meal/post-meal blood sugar based on the acquired skin image, user's body information, and measurement environment information to obtain the calculated multiple regression equation based on a user behavior pattern, the estimated blood sugar measured based on the acquired skin image, and measurement environment log data;
construct a blood sugar regression equation database that stores blood sugar regression equation data bias-adjusted according to the user's body information and the measurement environment information using the calculated multiple regression equation;
confirm the user's body information through image recognition;
estimate a meal time by analyzing the user behavior pattern and classifies the user's meal state into the pre-meal state or the post-meal state based on the estimated meal time; and
measure the robust blood sugar bias-adjusted according to the measurement environment information using the blood sugar regression equation, which is bias-adjusted according to the user's body information and the measurement environment information, and the acquired skin image.

20. A non-transitory computer-readable storage medium storing computer-executable instructions which cause, when executed by a processor, the processor to perform a method that includes:
calculating color data from multiple skin regions of interest in the skin image;
classifying a user's meal state into a pre-meal state or a post-meal state through analysis of acquired user information;
estimating blood sugar by applying the calculated color data to a blood sugar regression linear equation corresponding to the classified user's meal state; and
weighted averaging the estimated blood sugar to measure robust blood sugar.

* * * * *